(12) United States Patent
Chun

(10) Patent No.: US 9,250,202 B2
(45) Date of Patent: Feb. 2, 2016

(54) NANOPORE MOLECULE DETECTION SYSTEM AND MOLECULE DETECTION METHOD BASED ON POTENTIAL MEASUREMENT OF INSULATED CONDUCTIVE THIN LAYER

(71) Applicant: SNU R&DB FOUNDATION, Seoul (KR)

(72) Inventor: Honggu Chun, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 262 days.

(21) Appl. No.: 13/674,344

(22) Filed: Nov. 12, 2012

(65) Prior Publication Data

US 2013/0063168 A1    Mar. 14, 2013

Related U.S. Application Data

(63) Continuation-in-part of application No. PCT/KR2011/003527, filed on May 12, 2011.

(30) Foreign Application Priority Data

May 14, 2010   (KR) .................. 10-2010-0045419

(51) Int. Cl.
*G01N 27/00*    (2006.01)
*G01N 33/487*   (2006.01)

(52) U.S. Cl.
CPC .......... *G01N 27/00* (2013.01); *G01N 33/48721* (2013.01)

(58) Field of Classification Search
None
See application file for complete search history.

(56) References Cited

U.S. PATENT DOCUMENTS

| 7,005,264 B2 * | 2/2006 | Su et al. ................. 435/6.17 |
| 7,235,184 B2 * | 6/2007 | Dugas et al. ................. 216/2 |
| 8,262,879 B2 * | 9/2012 | Oliver ................. 204/450 |
| 8,794,054 B2 * | 8/2014 | Gridelet et al. ........... 73/61.61 |
| 2006/0073489 A1 | 4/2006 | Li et al. |

(Continued)

FOREIGN PATENT DOCUMENTS

| JP | 2006-113057 A | 4/2006 |
| KR | 10-2010-0040476 A | 4/2010 |

OTHER PUBLICATIONS

Nam, S-W. et al., "Ionic Field Effect Transistors with Sub-10 nm Multiple Nanopores," *Nano Letters*, 2009, pp. 2044-2048, vol. 9, No. 5. [Online] [Retrieved May 14, 2009] Retrieved from the Internet <URL:http://pubs.acs.org.>.

(Continued)

*Primary Examiner* — Minh N Tang
(74) *Attorney, Agent, or Firm* — Fenwick & West LLP

(57) ABSTRACT

A particle detector includes: a conductive nanolayer; insulating nanolayers attached to both sides of the conductive nanolayer; a nanopore formed to penetrate the conductive nanolayer and the insulating nanolayers so as to provide a migration path for a sample particle; a power supply unit configured to apply an electric field between both ends of the nanopore so as to apply a potential to the conductive nanolayer; and an electric signal measuring unit electrically connected to the conductive nanolayer and configured to measure the potential change in the conductive nanolayer induced by the sample particle as the sample particle migrates through the nanopore. The particle detector is capable of detecting a particle with high signal-to-noise ratio and resolution, scanning a sample without mechanical motion of the conductive nanolayer and analyzing DNA base sequences.

8 Claims, 7 Drawing Sheets

(56) References Cited

U.S. PATENT DOCUMENTS

| | | | |
|---|---|---|---|
| 2006/0086626 A1* | 4/2006 | Joyce | 205/792 |
| 2006/0231419 A1* | 10/2006 | Barth et al. | 205/775 |
| 2007/0178507 A1 | 8/2007 | Wu et al. | |
| 2008/0171316 A1* | 7/2008 | Golovchenko et al. | 435/6 |
| 2010/0084276 A1* | 4/2010 | Lindsay | 205/93 |
| 2011/0174620 A1 | 7/2011 | Choi et al. | |

OTHER PUBLICATIONS

Patent Cooperation Treaty, International Preliminary Report on Patentability, International Patent Application No. PCT/KR2011/003527, Nov. 20, 2012, 6 Pages.

Patent Cooperation Treaty, International Search Report, International Patent Application No. PCT/KR2011/003527, Feb. 6, 2012, 2 Pages.

* cited by examiner

NANOPORE MOLECULE DETECTION SYSTEM AND MOLECULE DETECTION METHOD BASED ON POTENTIAL MEASUREMENT OF INSULATED CONDUCTIVE THIN LAYER

CROSS-REFERENCE TO RELATED APPLICATION

This application is a continuation-in-part application of, and claims priority under 35 U.S.C. §365(c) and 35 U.S.C. 120 from, International Application No. PCT/KR2011/003527, designating the U.S. and filed on May 12, 2011, which claims priority to Republic of Korea Patent Application No. 10-2010-0045419, filed on May 14, 2010, which are incorporated herein in their entirety by reference.

BACKGROUND

1. Field

The present disclosure relates to a particle detector and a method for detecting a particle. More particularly, the disclosure relates to a particle detector and a method for detecting a particle based on nanopores, wherein a conductive nanolayer and nanopores are used, capable of detecting a particle with high signal-to-noise ratio and resolution and scanning a sample without mechanical movement of the conductive nanolayer.

2. Description of the Related Art

The most important performance indices in DNA (or RNA, hereinafter simply referred to as DNA) sequencing are read length and throughput. Recently, the direct DNA sequencing technique based on measurement of electrical current in nanopores or nanochannels is drawing attentions, because of its advantages of high spatial resolution, high throughput and theoretically unlimited read length.

The current measurement is performed axially or transversely. The axial current measurement is a method of measuring ionic current through the nanopores or nanochannels. Although the system configuration for the axial current measurement is relatively simple, deconvolution of signals is difficult because signals of a plurality of bases are obtained at once since the length of the nanopores or nanochannels is much longer than the distance between each DNA base, i.e. 0.33 nm. In the transverse current measurement, electrodes arranged perpendicularly to the nanopores or nanochannels are used to measure the change in tunneling current occurring as DNA passes between the electrodes. Although high spatial resolution can be achieved by the transverse current measurement, related procedures are relatively complicated.

Accordingly, for effective single-molecule DNA sequencing, development of an easier process and a highly sensitive detection system is necessary.

SUMMARY

An aspect of the present disclosure is directed to providing a particle detector and a method for detecting a particle based on nanopores, wherein a conductive nanolayer and nanopores are used, capable of detecting a particle with high signal-to-noise ratio and resolution and scanning a sample without mechanical movement of the conductive nanolayer.

According to an embodiment, the particle detector comprises: a conductive nanolayer; insulating nanolayers attached to both sides of the conductive nanolayer; a nanopore formed to penetrate the conductive nanolayer and the insulating nanolayers so as to provide a migration path for a sample particle; a power supply unit configured to apply an electric field between both ends of the nanopore so as to apply a potential to the conductive nanolayer; and an electric signal measuring unit electrically connected to the conductive nanolayer and configured to measure the potential change in the conductive nanolayer induced by the sample particle as the sample particle migrates through the nanopore.

The electric signal measuring unit may be configured to measure the potential change in the conductive nanolayer resulting from partial change in resistance in the nanopore caused by the sample particle or the potential change in the conductive nanolayer resulting from charge induced in the conductive nanolayer by the charge of the sample particle.

The conductive nanolayer may comprise a plurality of patterns separated from each other, and the nanopore may comprise a plurality of nanopores formed respectively in the plurality of patterns. The electric signal measuring unit may be configured to measure the potential change in the plurality of patterns independently.

The electric signal measuring unit may be configured to measure the potential change in the conductive nanolayer occurring sequentially as a single-stranded DNA (ssDNA) or a DNA to which a label is attached passes through the nanopore so as to analyze the base sequence of the DNA.

According to an embodiment, the method for detecting a particle comprises: providing a conductive nanolayer, insulating nanolayers attached to both sides of the conductive nanolayer, and a nanopore formed to penetrate the conductive nanolayer and the insulating nanolayers; applying a potential to the conductive nanolayer by applying an electric field between both ends of the nanopore; migrating a sample particle through the nanopore; and measuring the potential change in the conductive nanolayer induced by the sample particle as the sample particle migrates through the nanopore.

The measuring of the potential change in the conductive nanolayer may comprise measuring the potential change in the conductive nanolayer resulting from partial change in resistance in the nanopore caused by the sample particle or measuring the potential change in the conductive nanolayer resulting from charge induced in the conductive nanolayer by the charge of the sample particle.

The conductive nanolayer may comprise a plurality of patterns separated from each other, and the nanopore may comprise a plurality of nanopores formed respectively in the plurality of patterns. The measuring of the potential change in the conductive nanolayer may comprise measuring the potential change in the plurality of patterns independently.

The measuring of the potential change in the conductive nanolayer may comprise measuring the potential change in the conductive nanolayer occurring sequentially as an ssDNA or a DNA to which a label is attached passes through the nanopore so as to analyze the base sequence of the DNA.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Exemplary embodiments now will be described more fully hereinafter with reference to the accompanying drawings, in which exemplary embodiments are shown.

Figure 1A:
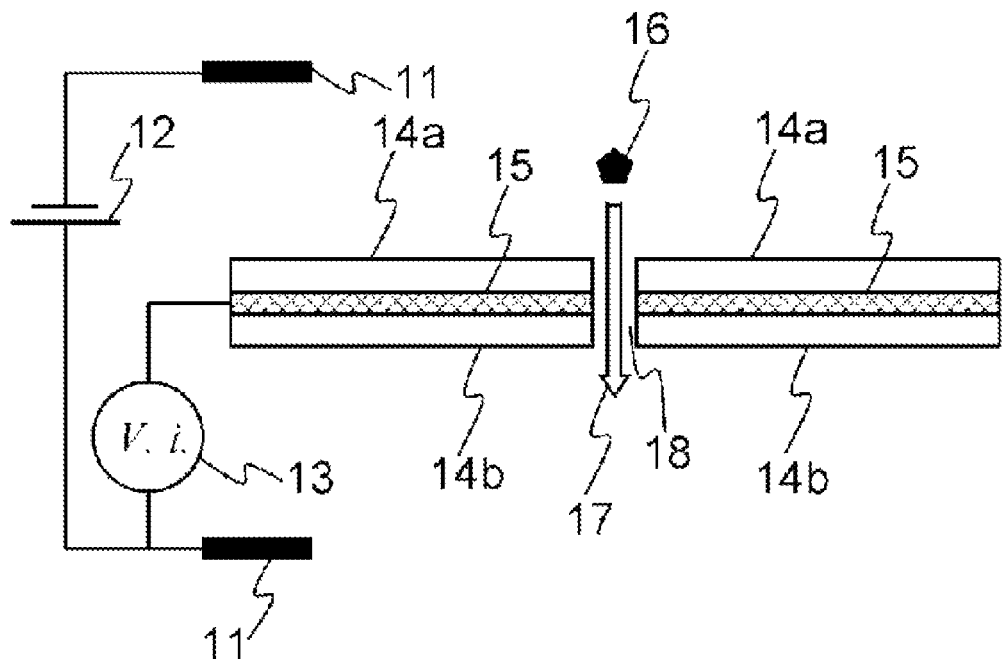
FIGS. 1A, 1B, 1C, and 1D are cross-sectional views for illustrating a particle detector according to an embodiment and signal measurement using the same.

FIGS. 1A, 1B, 1C, and 1D are cross-sectional views for illustrating a particle detector according to an embodiment and signal measurement using the same;

As shown in FIG. 1A, a particle detector according to an embodiment comprises a power supply unit 12, an electric signal measuring unit 13, insulating nanolayers 14a, 14b, a conductive nanolayer 15 and a nanopore 18. The particle detector may further comprise one or more electrodes 11.

The one or more electrodes 11 are used to apply an electric field by the power supply unit 12 between both ends of the nanopore 18. For this purpose, the one or more electrodes 11 may comprise a pair of electrodes separated from each other. The electrodes 11 may comprise a conducting material and may be electrically connected to the power supply unit 12. When a supply voltage is applied to the electrodes 11 from the power supply unit 12, an electric field may be applied between both ends of the nanopore 18. The insulating nanolayers 14a, 14b and the conductive nanolayer 15 may be disposed between the two electrodes 11.

The power supply unit 12 serves to apply an electric field between both ends of the nanopore 18. The power supply unit 12 may be a device for supplying a DC power. However, the present disclosure is not limited thereto, and the power supply unit 12 may be configured to supply AC or other type of power. As the power is supplied from the power supply unit 12, an electric field may be applied between both ends of the nanopore 18. Owing to the applied electric field, the conductive nanolayer 15 has a predetermined potential.

The electric signal measuring unit 13 may measure the potential change in the conductive nanolayer 15 induced by a sample particle 16 as the sample particle 16 migrates through the nanopore 18. For example, the electric signal measuring unit 13 may be configured to measure the potential change in the conductive nanolayer 15 resulting from charge induced in the conductive nanolayer 15 by the charge of the sample particle 16, the potential change in the conductive nanolayer 15 resulting from partial change in resistance in the nanopore 18 caused by the size of the sample particle 16, or both.

The insulating nanolayers 14a, 14b are thin films for insulating the conductive nanolayer 15. The insulating nanolayers 14a, 14b may be attached to both sides of the conductive nanolayer 15. That is to say, the insulating nanolayer 14a and the insulating nanolayer 14b may be respectively attached to different sides of the conductive nanolayer 15. In an embodiment, the insulating nanolayers 14a, 14b may have a thickness of about tens of nanometers. And, the insulating nanolayers 14a, 14b may comprise silicon nitride (SixNy) or titanium oxide (TiO2). However, the thickness or constituent material of the insulating nanolayers 14a, 14b is not limited to the above description but may be embodied variously so as to insulate the conductive nanolayer 15 from its surrounding medium.

The conductive nanolayer 15 is a thin film for detecting potential change resulting from charge induced by the charge of the sample particle 16 or partial change in resistance in the nanopore 18 caused by the size of the sample particle 16. Alternatively, potential change resulting from charge induced in the conductive nanolayer 15 by the charge of the sample particle 16 may be detected through the conductive nanolayer 15. In an embodiment, the conductive nanolayer 15 may have a thickness of not greater than tens of nanometers. And, the conductive nanolayer 15 may comprise gold (Au), graphene or titanium nitride (TiN). However, this is only exemplary and the thickness or constituent material of the conductive nanolayer 15 is not limited to the above description but may be embodied variously.

The nanopore 18 is a migration path through which the sample particle 16 can be introduced. The nanopore 18 may be formed to penetrate the conductive nanolayer 15 and the insulating nanolayers 14a, 14b. As used herein, the nanopore refers to an aperture of a nanometer scale that can serves as a migration path through which a sample particle can pass and is not particularly limited in size or shape. For example, the diameter of the nanopore 18 may be determined according to the size of the sample particle 16 to be detected. The diameter of the nanopore 18 may be smaller than 10 times the diameter of the sample particle 16. The nanopore may be any structure allowing the migration of the sample particle, without being limited in preparation method or name. For example, the nanopore referred to in this disclosure may be also referred to as a nanochannel.

The sample particle 16 is a substance to be detected using a particle detector according to an embodiment. For example, the sample particle 16 may comprise a DNA or an RNA. Also, the DNA may be either a single-stranded DNA (ssDNA) obtained from a naturally occurring DNA or a DNA to which a label is attached.

FIG. 1A shows a state before the sample particle 16 is introduced to the nanopore 18 of the particle detector according to an embodiment. In this state, the electric signal measuring unit 13 obtains a constant value. That is to say, the conductive nanolayer 15 may have a predetermined potential which is determined by the arrangement of the conductive nanolayer 15 between the two electrodes 11 to which the electric field is applied and the power supplied from the power supply unit 12.

Figure 1B:
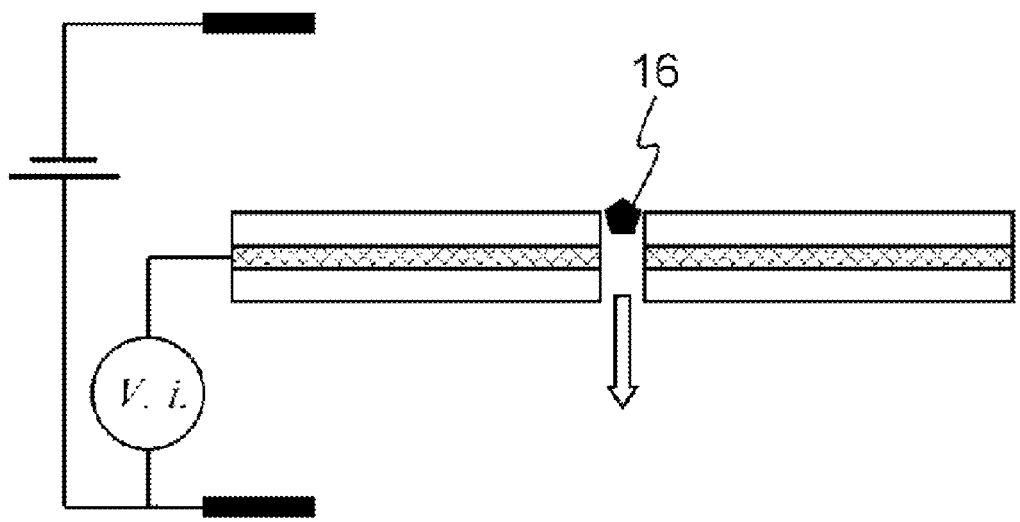

FIG. 1B shows an early state where the sample particle 16 is introduced into the nanopore 18 of the particle detector according to an embodiment. As the sample particle 16 blocks the upper portion of the nanopore 18, the portions of the nanopore 18 above and below the conductive nanolayer 15 have different resistance. Consequently, potential change occurs in the conductive nanolayer 15 and this value is detected by the electric signal measuring unit 13.

Figure 1C:
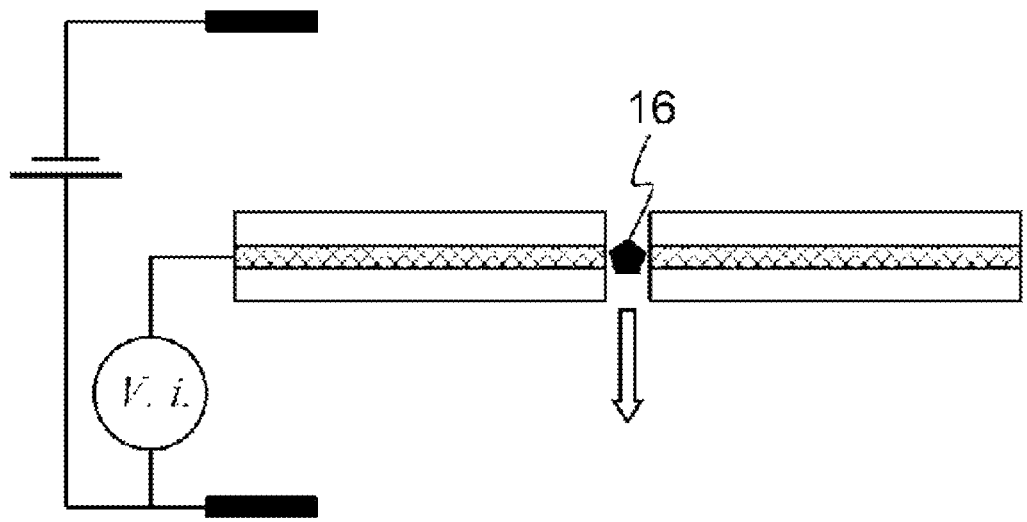

FIG. 1C shows a state where the sample particle 16 migrates further downward through the nanopore 18 and is positioned near the conductive nanolayer 15. In this state, the portions of the nanopore 18 above and below the conductive nanolayer 15 have similar resistance. Meanwhile, potential change in the conductive nanolayer 15 resulting from charge induced in the conductive nanolayer 15 by the charge of the sample particle 16 may be detected by the electric signal measuring unit 13.

Figure 1D:
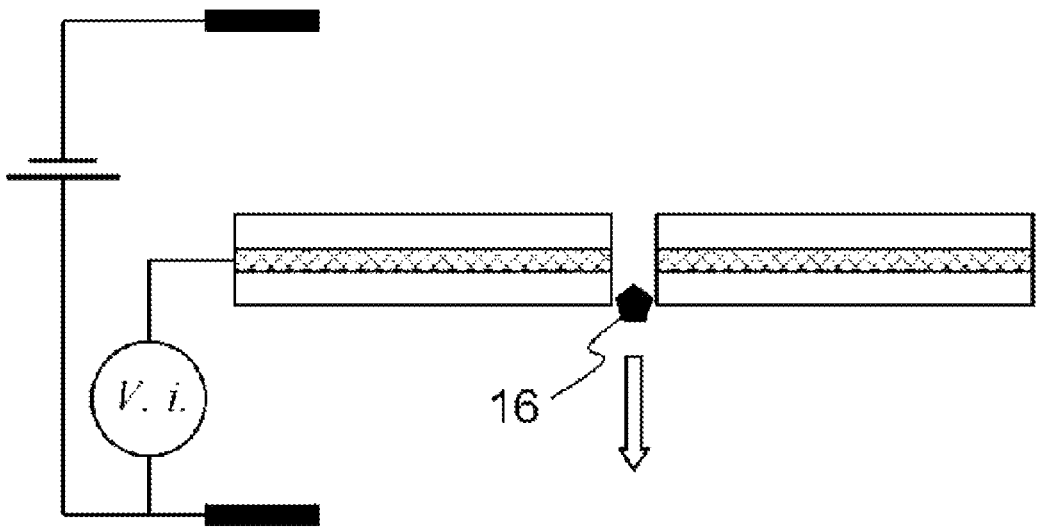

FIG. 1D shows a state where the sample particle 16 migrates further downward through the nanopore 18 and is positioned at the lower portion of the nanopore 18. In this state, since the sample particle 16 blocks the lower portion of the nanopore 18, the portions of the nanopore 18 above and below the conductive nanolayer 15 have different resistance. Consequently, potential change occurs in the conductive nanolayer 15 and this value is detected by the electric signal measuring unit 13. Thereafter, the sample particle 16 leaves the nanopore 18.

As described above, potential change occurs in the conductive nanolayer 15 while the sample particle 16 migrates through the nanopore 18. The potential change in the conductive nanolayer 15 depends on the partial change in resistance in the nanopore 18 caused by the size of the sample particle 16 and/or the charge induced in the conductive nanolayer 15 by the charge of the sample particle 16. Accordingly, the sample particle 16 migrating through the nanopore 18 may be identified and detected by measuring the potential change in the conductive nanolayer 15.

FIGS. 2A through 2H show a process of fabricating a particle detector according to an embodiment. FIGS. 2A, 2C, 2E and 2G are cross-sectional views for illustrating a process of fabricating the particle detector. And, FIGS. 2B, 2D, 2F and 2H are plan views of FIGS. 2A, 2C, 2E and 2G, respectively.

A particle detector according to an embodiment shown in FIGS. 2A through 2H has a structure wherein a conductive nanolayer 15 comprises a plurality of patterns separated from each other and a nanopore 18 is formed for each separated pattern, such that sample particles 16 migrating through the nanopores 18 are detected in parallel by an electric signal measuring unit 13 electrically connected to the respective patterns. That is to say, the plurality of nanopores 18 are arranged in an array to form a nanopore array.

Figure 2A:
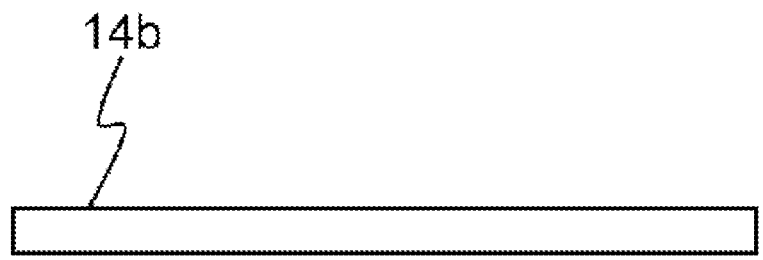
FIG. 2A is a cross-sectional view showing a process of fabricating a particle detector according to an embodiment.
Figure 2B:
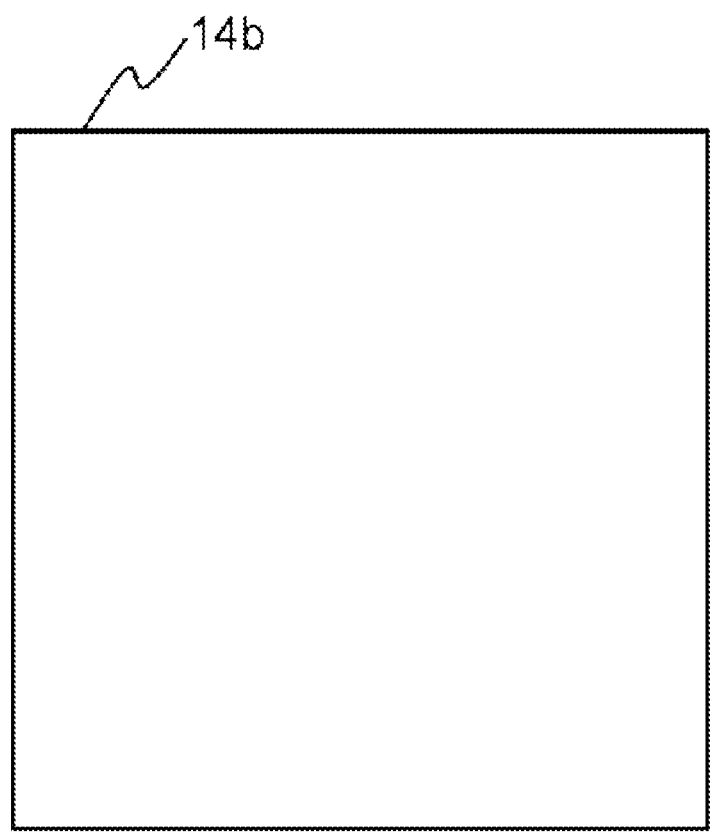
FIG. 2B is a plan view of FIG. 2A.

Referring to FIGS. 2A and 2B, an insulating nanolayer 14b may be prepared. The insulating nanolayer 14b is to be attached to the surface of a conductive nanolayer which will be formed later for insulation.

Figure 2C:
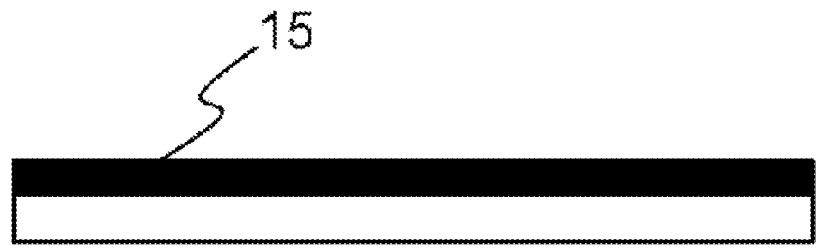
FIG. 2C is a cross-sectional view showing a process of fabricating a particle detector according to an embodiment.
Figure 2D:
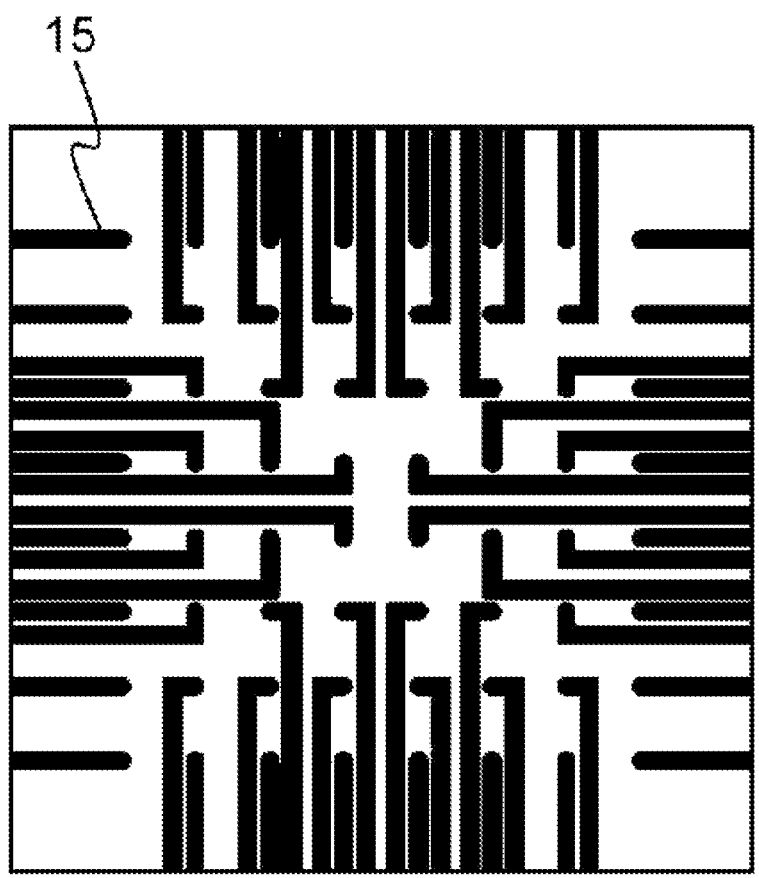
FIG. 2D is a plan view of FIG. 2C.

Referring to FIGS. 2C and 2D, a conductive nanolayer 15 may be formed on the insulating nanolayer 14b. The conductive nanolayer 15 may comprise a plurality of patterns separated from each other. FIG. 2D shows a conductive nanolayer 15 comprising 64 independent patterns. However, this is only exemplary and the conductive nanolayer 15 may comprise patterns of different number and shape. Alternatively, in an embodiment, the conductive nanolayer 15 may comprise a single layer.

Figure 2E:
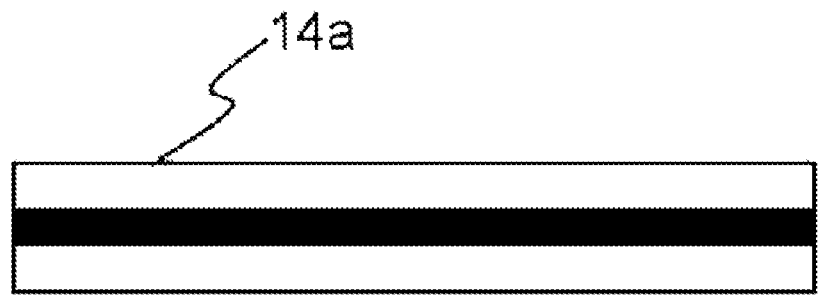
FIG. 2E is a cross-sectional view showing a process of fabricating a particle detector according to an embodiment.
Figure 2F:
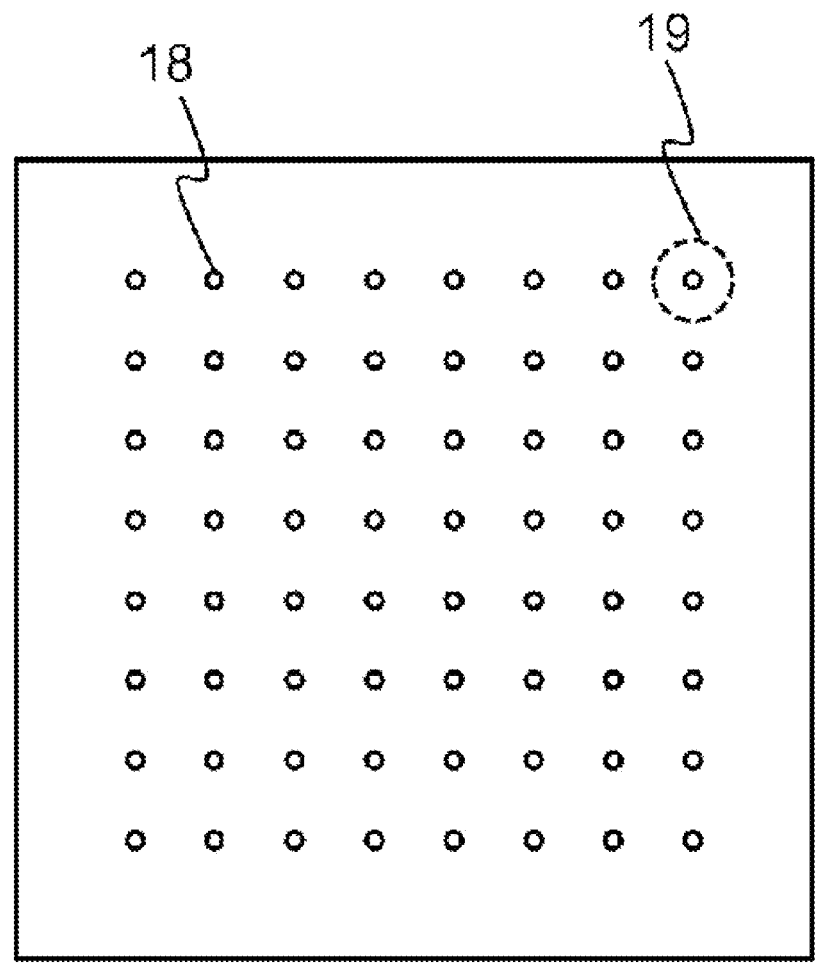
FIG. 2F is a plan view of FIG. 2E.

Referring to FIGS. 2E and 2F, an insulating nanolayer 14a may be formed on the conductive nanolayer 15. Also, a nanopore 18 may be formed corresponding to each pattern of the conductive nanolayer 15. However, this is only exemplary and the number of the patterns of the conductive nanolayer 15 may not be necessarily the same as that of the nanopores 18 in another embodiment.

Figure 2G:
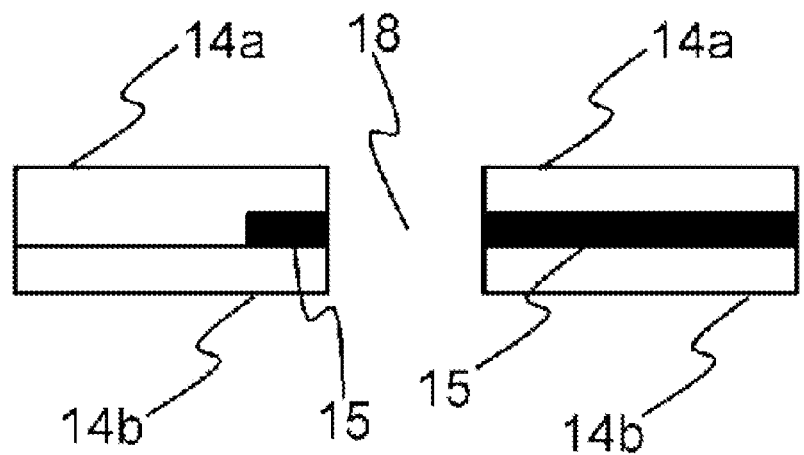
FIG. 2G is a cross-sectional view showing a process of fabricating a particle detector according to an embodiment.
Figure 2H:
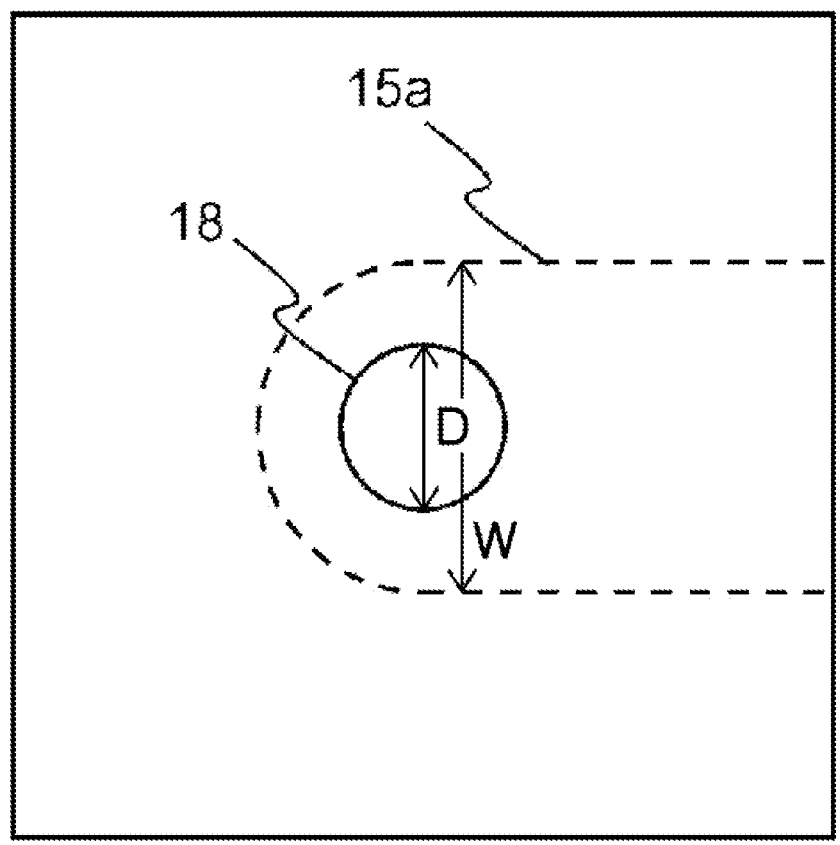
FIG. 2H is a plan view FIG. 2G.

FIGS. 2G and 2H are magnified views of a portion 19 of the nanopore array shown in FIG. 2F. As seen from the figures, the nanopores 18 may be formed to penetrate the patterned conductive nanolayer 15 and the insulating nanolayers 14a, 14b attached thereto. Referring to FIG. 2H, in an embodiment, the diameter D of the nanopore 18 may be smaller than the width W of the pattern 15a of the conductive nanolayer where the nanopore 18 is located.

The particle detector described referring to FIGS. 2A through 2H is advantageous in that independent signal measurement is possible for each nanopore 18. That is to say, it is possible to independently detect particles passing through the plurality of nanopores 18 of the nanopore array. Accordingly, high-speed particle detection can be achieved through parallel signal acquisition.

Figure 3:
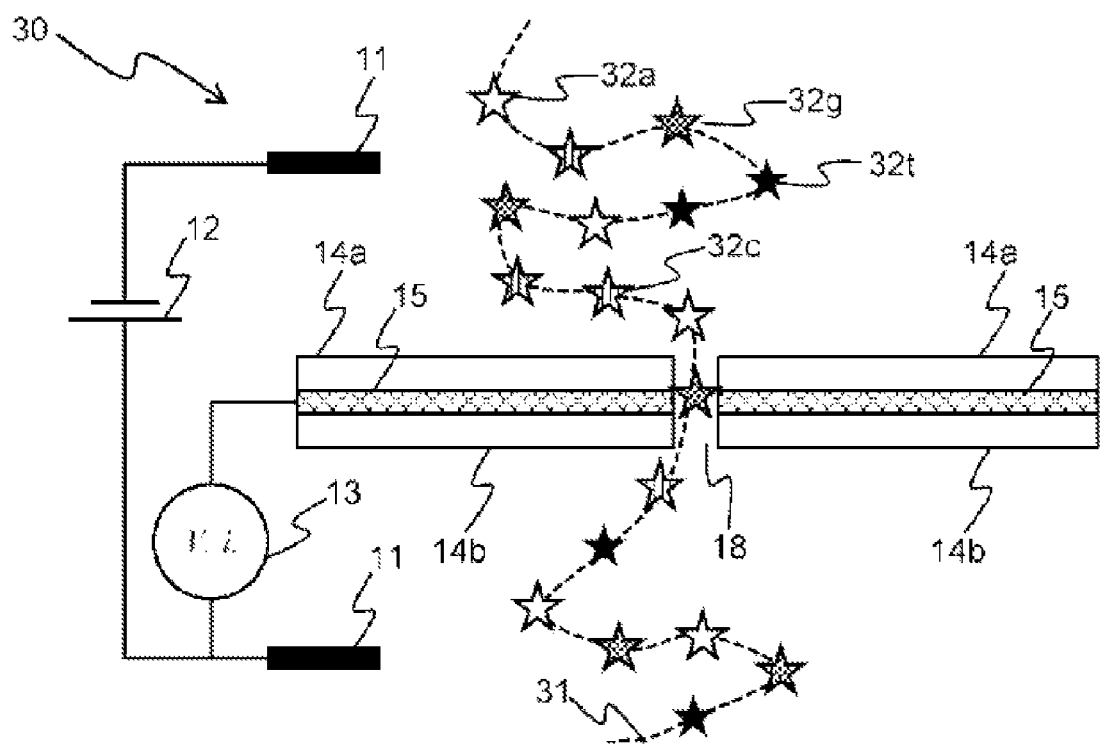
FIG. 3 is a schematic view for illustrating DNA base sequencing using a particle detector according to an embodiment.

FIG. 3 is a schematic view for illustrating DNA base sequencing using a particle detector according to an embodiment.

Referring to FIG. 3, in a particle detector according to an embodiment, a DNA may be passed through a nanopore formed in a conductive nanolayer to which an electric signal measuring unit is connected, while reading sequentially generated electric signals so as to analyze the base sequence of the DNA. The particle detector for DNA base sequencing may comprise electrodes 11, a power supply unit 12, an electric signal measuring unit 13, insulating nanolayers 14a, 14b, a conductive nanolayer 15 and a nanopore 18. Detailed description of the configuration of the particle detector will be omitted since it is the same as in the foregoing embodiment described referring to FIG. 1A.

For DNA base sequencing, a DNA 31 is used as a sample particle. The DNA 31 may be an ssDNA obtained from a naturally occurring DNA. Alternatively, the DNA 31 may have labels 32a, 32g, 32t, 32c attached thereto. The labels 32a, 32g, 32t, 32c are attached to the DNA 31 to give electric signals corresponding to the adenine (A), guanine (G), thymine (T) and cytosine (C) bases, respectively, and may have different charge or size.

Since the distance between each base of the DNA 31 is only about 0.33 nm, it is difficult to label all the bases. Accordingly, the labels may be attached at specific intervals. Alternatively, the target DNA may be augmented using the designed DNA polymer technique and the labels 32a, 32g, 32c, 32t corresponding to the bases may be attached, such that the labels 32a, 32g, 32t, 32c are separated from each other with predetermined intervals. Detailed description about the designed DNA polymer technique will be omitted since it is well known to those skilled in the art.

As described above, in accordance with the present disclosure wherein the conductive nanolayer and the nanopore are used, a particle can be detected with high signal-to-noise ratio and resolution and a sample can be scanned without mechanical motion of the conductive nanolayer using the nanopore-based particle detector. Also, DNA base sequencing can be achieved by passing a DNA through the nanopore and analyzing the signals read by the electric signal measuring unit.

In the future, the medical services will become more prognostic, preventive and customized. To realize such medical services, base sequencing for obtaining genetic information at low cost is required. The DNA sequencing according to the present disclosure is applicable to personal genomics required for these medical services. Also, the method for detecting a particle based on potential measurement of the insulated thin-film electrode is applicable to various clinical diagnoses or sensors since it allows effective detection of nanoparticles.

While the exemplary embodiments have been shown and described, it will be understood by those skilled in the art that various changes in form and details may be made thereto without departing from the spirit and scope of the present disclosure as defined by the appended claims.

What is claimed is:

1. A particle detector comprising:
    a single conductive nanolayer;
    insulating nanolayers attached to both sides of the conductive nanolayer;
    a nanopore formed to penetrate the conductive nanolayer and the insulating nanolayers so as to provide a migration path for a sample particle;
    a power supply unit comprising a pair of electrodes configured to apply an electric field between both ends of the nanopore so as to apply a potential between the single conductive nanolayer and one of the pair of electrodes, wherein the potential between the single conductive nanolayer and the one of the pair of electrodes is determined by spatial arrangement of the single conductive nanolayer between the pair of electrodes and power supplied from the power supply unit to the pair of electrodes; and an electric signal measuring unit electrically connected to one end of the single conductive nanolayer and configured to measure a change in the potential between the single conductive nanolayer and the one of the pair of electrodes to which the power is supplied, wherein the change in the potential between the single conductive nanolayer and the one of the pair of electrodes is induced by a resistance change of the nanopore above and below the sample particle as the sample particle migrates through the nanopore.

2. The particle detector according to claim 1, wherein the single conductive nanolayer comprises graphene.

3. A particle detector comprising:
a single conductive nanolayer;
insulating nanolayers attached to both sides of the conductive nanolayer;
a nanopore formed to penetrate the conductive nanolayer and the insulating nanolayers so as to provide a migration path for a sample particle;
a power supply unit comprising a pair of electrodes configured to apply an electric field between both ends of the nanopore so as to apply a potential between the single conductive nanolayer and one of the pair of electrodes, wherein the potential between the single conductive nanolayer and the one of the pair of electrodes is determined by spatial arrangement of the single conductive nanolayer between the pair of electrodes and power supplied from the power supply unit to the pair of electrodes; and
an electric signal measuring unit electrically connected to the single conductive nanolayer and configured to measure a change in the potential between the single conductive nanolayer and the one of the pair of electrodes to which the power is supplied, wherein the change in potential between the single conductive nanolayer and the one of the pair of electrodes is induced by a resistance change of portions of the nanopore above and below the sample particle as the sample particle migrates through the nanopore,
wherein the conductive nanolayer comprises a plurality of patterns separated from each other, the nanopore comprises a plurality of nanopores formed respectively in the plurality of patterns, and the electric signal measuring unit is electrically connected to one end of each of the plurality of patterns and is configured to measure the potential change in the plurality of patterns independently.

4. The particle detector according to claim 1, wherein the electric signal measuring unit is configured to measure the potential change in the conductive nanolayer occurring sequentially as a single-stranded DNA (ssDNA) passes through the nanopore so as to analyze the base sequence of the DNA.

5. A method for detecting a particle, comprising:
providing a single conductive nanolayer, insulating nanolayers attached to both sides of the conductive nanolayer, and a nanopore formed to penetrate the conductive nanolayer and the insulating nanolayers;
applying a potential to the single conductive nanolayer by applying an electric field between both ends of the nanopore using a pair of electrodes electrically connected to a power supply unit and having the single conductive nanolayer disposed therebetween, wherein a potential between the single conductive layer and one of the pair of electrodes is determined by spatial arrangement of the single conductive nanolayer between the pair of electrodes and power supplied from the power supply unit to the pair of electrodes;
migrating a sample particle through the nanopore; and
measuring, by an electric signal measuring unit electrically connected to one end of the single conductive nanolayer, a change in the potential between the single conductive nanolayer and the one of the pair of electrodes to which the power is supplied, wherein the change in the potential between the single conductive nanolayer and the one of the pair of electrodes is induced by a resistance change of portions of the nanopore above and below the sample particle as the sample particle migrates through the nanopore.

6. The method for detecting a particle according to claim 5, wherein the single conductive nanolayer comprises graphene.

7. The method for detecting a particle according to claim 5, wherein said measuring the potential change in the single conductive nanolayer comprises measuring the potential change in the single conductive nanolayer occurring sequentially as a single-stranded DNA (ssDNA) passes through the nanopore so as to analyze the base sequence of the DNA.

8. A method for detecting a particle, comprising:
providing a single conductive nanolayer, insulating nanolayers attached to both sides of the conductive nanolayer, and a nanopore formed to penetrate the conductive nanolayer and the insulating nanolayers;
applying a potential to the single conductive nanolayer by applying an electric field between both ends of the nanopore using a pair of electrodes electrically connected to a power supply unit and having the single conductive nanolayer disposed therebetween, wherein a potential between the single conductive nanolayer and one of the pair of electrodes is determined by spatial arrangement of the single conductive layer between the pair of electrodes and power supplied from the power supply unit to the pair of electrodes;
migrating a sample particle through the nanopore; and
measuring a change in the potential between the single conductive nanolayer and the one of the pair of electrodes to which the power is supplied, wherein the change in the potential between the single conductive nanolayer and the one of the pair of electrodes is induced by a resistance change of portions of the nanopore above and below the sample particle as the sample particle migrates through the nanopore,
wherein the single conductive nanolayer comprises a plurality of patterns separated from each other, the nanopore comprises a plurality of nanopores formed respectively in the plurality of patterns, and said measuring the potential change in the conductive nanolayer comprises measuring, by an electric signal measuring unit electrically connected to one end of each of the plurality of patterns, the potential change in the plurality of patterns independently.

* * * * *